United States Patent
Mayenberger

(10) Patent No.: US 6,558,384 B2
(45) Date of Patent: May 6, 2003

(54) SURGICAL BIPOLAR SCISSORS

(75) Inventor: Rupert Mayenberger, Rielasingen (DE)

(73) Assignee: Aesculap AG & Co. KG, Tuttlingen (DE)

(*) Notice: Subject to any disclaimer, the term of this patent is extended or adjusted under 35 U.S.C. 154(b) by 27 days.

(21) Appl. No.: 09/871,147

(22) Filed: May 29, 2001

(65) Prior Publication Data

US 2002/0019632 A1 Feb. 14, 2002

Related U.S. Application Data

(63) Continuation of application No. PCT/EP99/08857, filed on Nov. 18, 1999.

(30) Foreign Application Priority Data

Dec. 3, 1998 (DE) .......................... 198 55 812

(51) Int. Cl.[7] .............................................. A61B 18/18
(52) U.S. Cl. ............................. 606/48; 606/45; 606/50
(58) Field of Search .............................. 606/41, 46, 47, 606/48–52

(56) References Cited

U.S. PATENT DOCUMENTS

| 5,324,289 | A |   | 6/1994  | Eggers |        |
|-----------|---|---|---------|--------|--------|
| 5,573,534 | A |   | 11/1996 | Stone  |        |
| 5,779,701 | A | * | 7/1998  | McBrayer et al. | 606/46 |
| 5,951,549 | A | * | 9/1999  | Richardson et al. | 606/45 |
| 5,954,720 | A |   | 9/1999  | Wilson et al. |  |
| 6,193,718 | B1 | * | 2/2001 | Kortenbach et al. | 606/50 |
| 6,334,861 | B1 | * | 1/2002 | Chandler et al. | 606/50 |

FOREIGN PATENT DOCUMENTS

| EP | 0 572 131 | 12/1993 |
| EP | 0 850 598 | 7/1998  |

* cited by examiner

*Primary Examiner*—Linda C. M. Dvorak
*Assistant Examiner*—David M. Ruddy
(74) *Attorney, Agent, or Firm*—Barry R. Lipsitz; Douglas M. McAllister

(57) ABSTRACT

In order to improve the cutting properties of surgical bipolar scissors with two scissor blades pivotable relative to each other, the first of which consists of an electrically conductive material and the second of an electrically insulating material on the side thereof facing the first scissor blade, but of an electrically conductive material on the side facing away from the first scissor blade, it is proposed that the second scissor blade comprise a ceramic shaped body in the form of a complete scissor blade which extends beyond a bearing point of the two scissor blades, that a metallic support blade which similarly extends beyond the bearing point rest against the outer side of the shaped body over the surface thereof, and that the shaped body and the support blade be permanently connected to each other at their contact surface.

7 Claims, 4 Drawing Sheets

SURGICAL BIPOLAR SCISSORS

Figure 1:
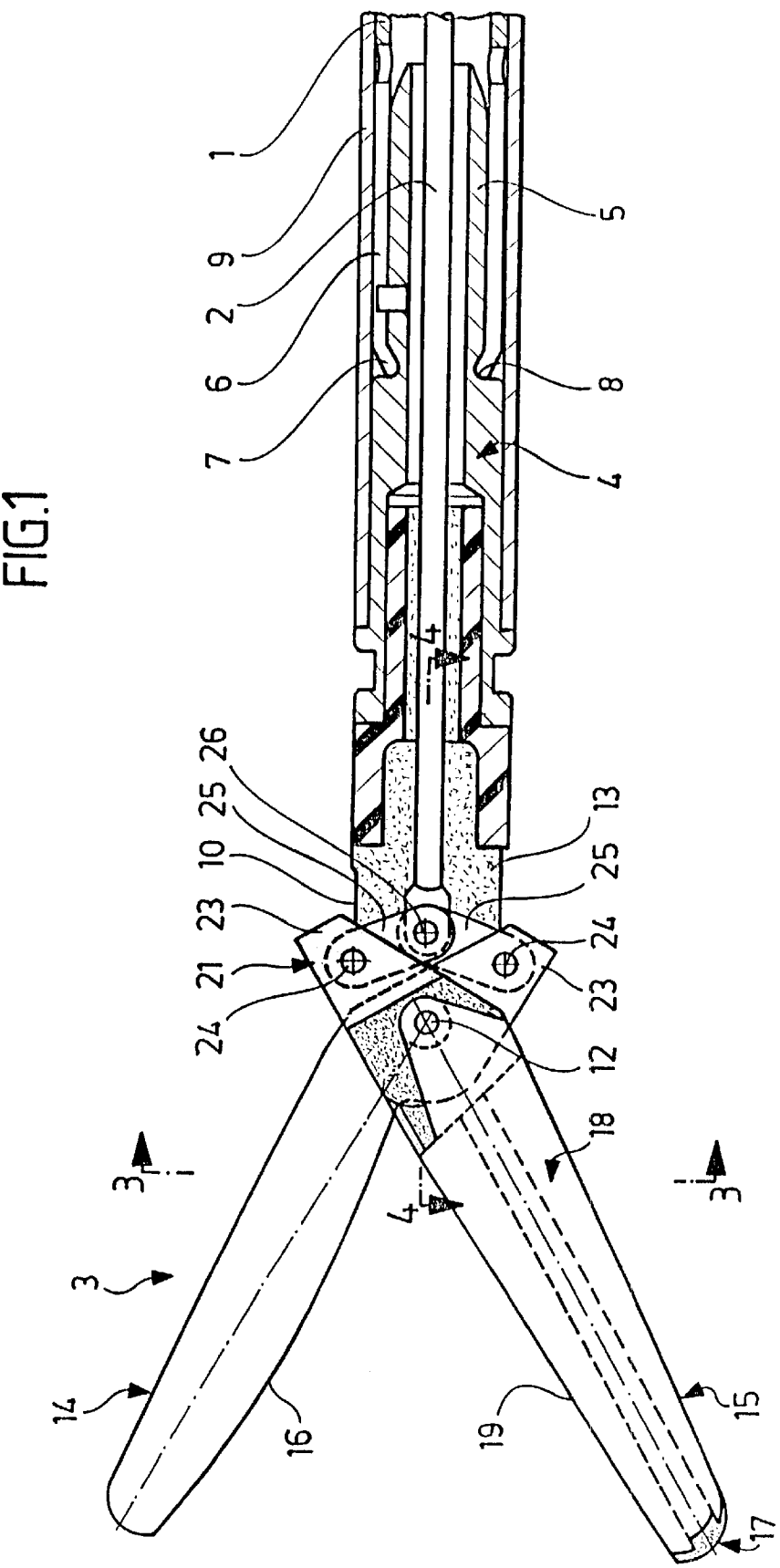

The present invention relates to the subject matter disclosed in international application PCT/EP 99/08857 of Nov. 18, 1999, the entire specification of which is incorporated herein by reference.

The invention relates to surgical bipolar scissors with two scissor blades pivotable relative to each other, the first of which consists of an electrically conductive material and the second of an electrically insulating material on the side thereof facing the first scissor blade, but of an electrically conductive material on the side thereof facing away from the first scissor blade.

Surgical bipolar scissors of this kind are known, for example, from U.S. Pat. No. 5,324,289. With bipolar scissors of this design it is possible to make hemostatic incisions, i.e., upon applying an alternating voltage to the two electrically conductive parts of the two scissor blades a current flows in the area of the incision point between these and owing to the provision of an insulating layer on the one scissor blade it does not run directly from scissor blade to scissor blade, but through the tissue positioned in the area of the incision point in which bleeding can in this way be stopped.

In the known surgical bipolar scissors, insulating materials are disposed on one of the two scissor blades in the cutting area, for example, by means of coating in a gas stream or by applying thin ceramic layers which are joined to the metallic scissor blade.

Starting from this prior art, the object underlying the invention is to design surgical bipolar scissors so that these are, on the one hand, particularly effective, and, on the other hand, particularly stable in the cutting edge area.

This object is accomplished with surgical bipolar scissors of the kind described at the outset in accordance with the invention in that the second scissor blade comprises a ceramic shaped body in the form of a complete scissor blade extending beyond a bearing point of the two scissor blades, in that a metallic support blade likewise extending beyond the bearing point rests against the outer side of the shaped body over the surface thereof, and in that the shaped body and the support blade are permanently connected to each other at their contact surface.

In contrast to known bipolar scissors, the second scissor blade itself is constructed as a ceramic shaped body so that a metallic scissor blade is located opposite a scissor blade consisting of a ceramic material in the tool area, and these two parts together perform the cutting operation.

An additional support blade is provided for stabilizing the ceramic shaped body and forming a counter electrode for the metallic scissor blade. The support blade is positioned on the outer side of the ceramic shaped body and is connected thereto over the surface thereof. Both the ceramic shaped body and the support blade on the outer side thereof extend beyond the bearing point of the scissor blade so that the supporting action of the support blade becomes effective precisely in this area which is subjected to very high mechanical stress.

Provision may be made in a preferred embodiment for the shaped body to form a bearing sleeve which surrounds a bearing shaft of the two scissor blades and extends through the first scissor blade. A complete insulation of the two scissor blades from each other is thereby ensured, also in the bearing area. It is thus possible to use a bearing shaft made of a conductive material, in particular, a metallic bearing shaft, which can then also be simultaneously used as electrical connection of the support blade to a connection of a voltage source.

Provision is made in a preferred embodiment for the shaped body and the support blade to comprise projections and recesses which engage one another in a positively locking manner. Owing to this positive locking connection, the ceramic shaped body is supported optimally so that the surface connection between shaped body, on the one hand, and support blade, on the other hand, is maintained even under high stress.

In particular, provision may be made for the shaped body to carry a longitudinal rib which engages in a longitudinal groove of the support blade in a positively locking manner. The longitudinal rib and the longitudinal groove preferably extend over the entire length of the shaped body.

Further provision may be made for a metal extension element to rest against the shaped body in the area of the bearing point thereof on the side thereof opposite the support blade and to be connected to the shaped body. The extension element is, in turn, connected to a part of a pivot mechanism for pivoting the scissor blades. The pivot mechanism has to transmit large forces and so it is expedient to use metal as material therefor, but this metal is electrically insulated from the support blade by the shaped body interposed therebetween, so that it is ensured that an electrical connection does not occur between the pivot mechanism, on the one hand, and the support blade, on the other hand.

It is expedient for the shaped body and the extension element to comprise projections and recesses engaging one another in a positively locking manner so that the connection between the two parts is thereby also stabilized, in particular, for the transmission of the pivoting moments.

The shaped body and the support blade can be joined surface-to-surface to one another in any chosen way. In particular, they are soldered to each other.

It is expedient for the shaped body and the support blade to be connected to each other in the cutting area by a soft solder, in the area of the bearing point by a hard solder.

As a whole, one thus obtains a sandwich-like second scissor blade which is made up of the shaped body and the support blade and which like the first scissor blade can be inserted as a structural unit into the surgical instrument.

Figure 2:
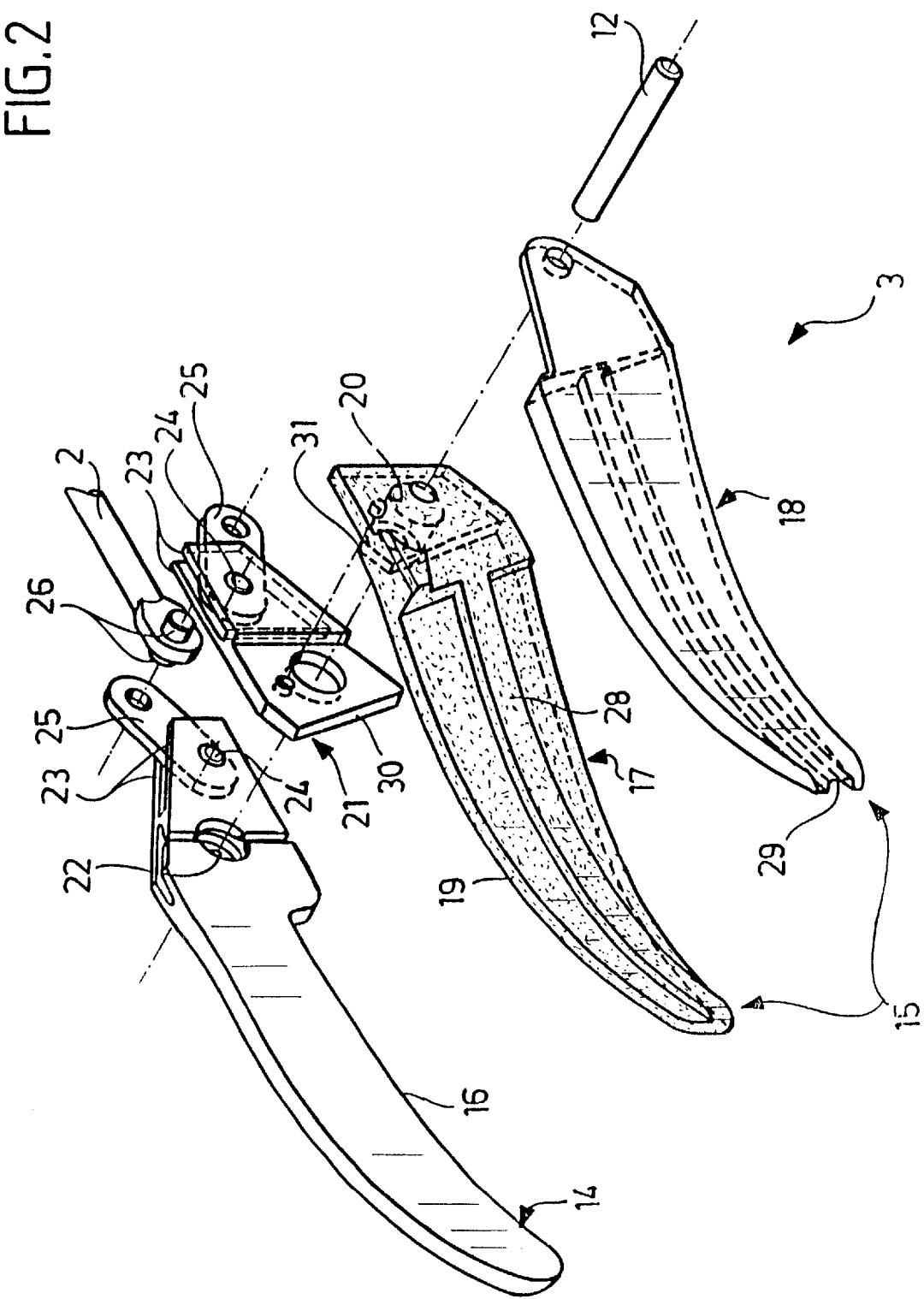
Figure 3:
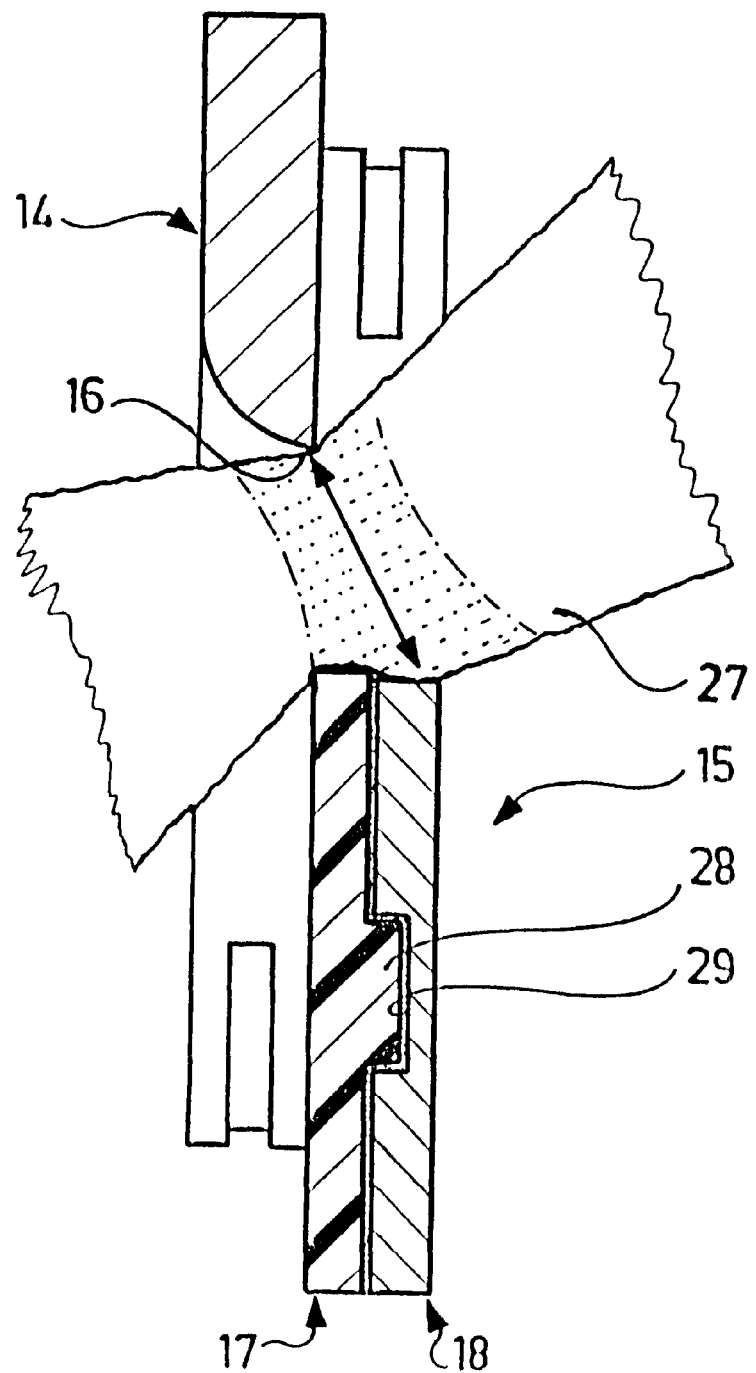
Figure 4:
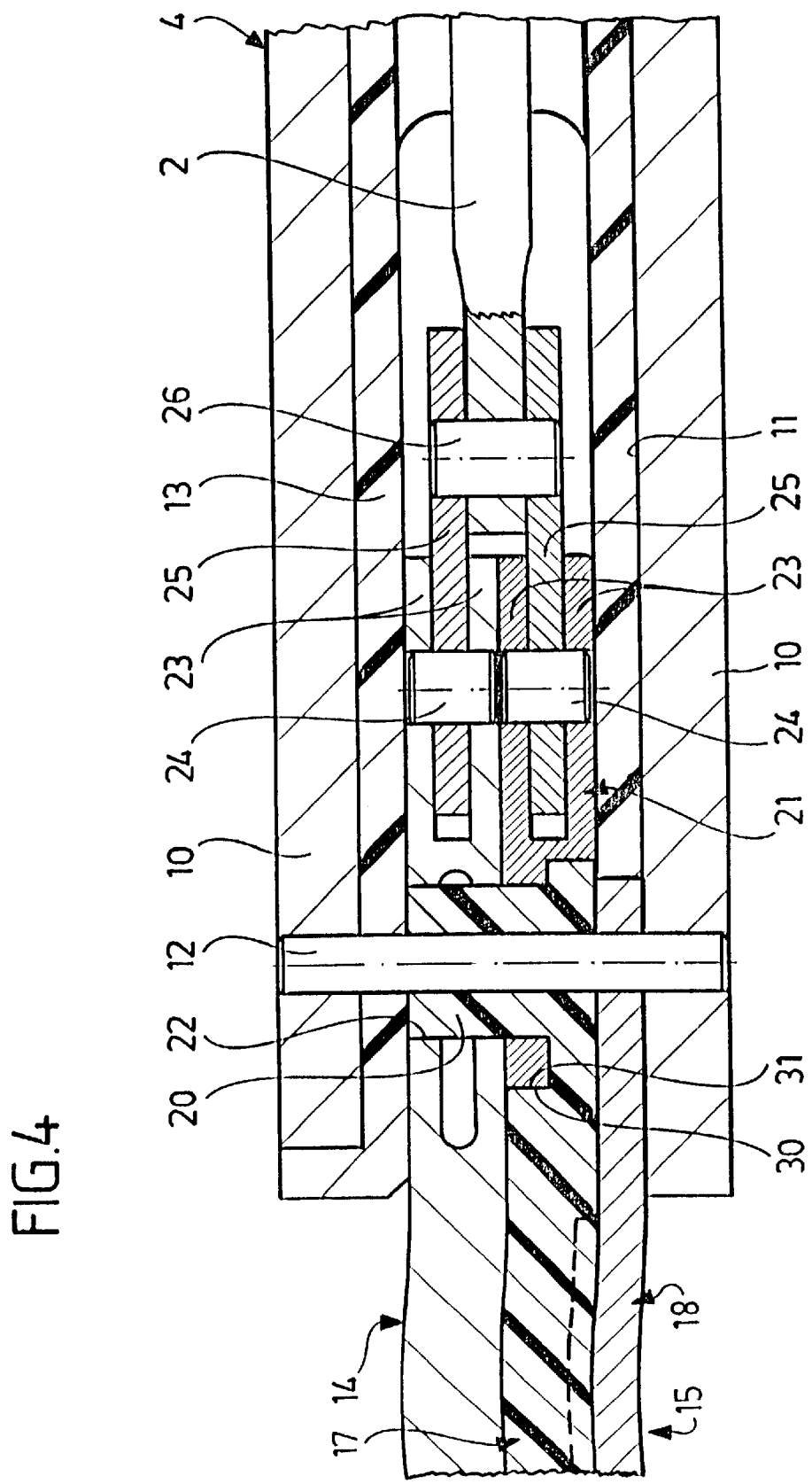

The following description of preferred embodiments serves in conjunction with the drawings for further explanation. The drawings show:

| | |
|---|---|
| FIG. 1 | a longitudinal sectional view through the tool-side end of a bipolar cutting element with open scissor blades; |
| FIG. 2 | an exploded view of the parts forming the cutting tool; |
| FIG. 3 | a sectional view along line 3-3 in FIG. 1 with tissue disposed between the scissor blades; and |
| FIG. 4 | a sectional view along line 4-4 in FIG. 1. |

The bipolar scissors shown in the drawings are constructed as a tubular shaft instrument, only the front, i.e., cutting, area of which is illustrated in the drawings. Such tubular shaft instruments comprise an elongate, tubular shaft 1, in which a push-pull rod 2 is reciprocatingly displaceable. At the rear end, not shown in the drawings, there is a handle with two handle members movable relative to each other. When moved accordingly, these push the push-pull rod back and forth within the shaft.

A tool 3 is arranged at the front end of the shaft 1, i.e., at the end thereof located opposite the handle. The tool 3 is mounted on a holder 4 which is inserted at its end face in the shaft 1 by means of a hollow insert pin 5. In the inserted state, the insert pin 5 is fixed by spring-tongue-shaped portions 6 of the shaft 1, which dip with their free ends 7 into an annular groove 8 of the insert pin 5 and are fixed in this position by a sleeve 9 embracing the shaft 1.

The holder 4 forms in its portion protruding from the shaft 1 two parallel arms 10 which are joined together at their free end by a bearing shaft 12 bridging the space 11 between the arms 10. The holder 4 and the bearing shaft 12 consist of metal and so are electrically conductive. On their inner sides, the arms 10 have an electrically insulating coating 13 which also continues into the hollow interior of the insert pin 5.

The tool 3 comprises two scissor blades 14 and 15, which are mounted by means of the bearing shaft 12 on the holder 4 for pivotal movement relative to each other.

The first scissor blade 14 consists of metal, for example, stainless steel. It is slightly bent and forms a cutting edge 16 on its lower side.

The second scissor blade 15 is in the form of a composite body and comprises a scissor-blade-type shaped body 17 made of ceramics, in particular, of injected ceramics, and a metallic support blade 18 adapted in its shape to the shaped body 17 and resting with its outer side on the shaped body 17 over the surface thereof. The shaped body 17 forms the actual cutting element, and the upper edge of the shaped body 17 forms a cutting edge 19 which cooperates with the cutting edge 16 of the first scissor blade 14. This cutting edge 19 is normally of blunt design, for example, when an angle of the scissor blades of between 80 and 90° is used.

The shaped body 17 bears at its rear end an integrally formed sleeve 20 protruding at right angles from the plane of the shaped body 17. The sleeve 20 surrounds the bearing shaft 12 and thus forms a pivot bearing for the shaped body 17. This sleeve 20 projects through a plate-shaped extension element 21 which in the area of the bearing point rests surface-to-surface against the shaped body 17, thereby surrounding the sleeve 20, namely on the side of the shaped body 17 remote from the support blade 18 so that the shaped body 17 is embedded in the bearing area between the metallic support blade 18 and the similarly metallic extension element 21.

The sleeve 20 also projects through a bearing opening 22 in the rear end of the first scissor blade 14, which is thereby mounted on the holder 4 for pivotal movement on the sleeve 20 and hence concentrically to the bearing shaft 12.

Both the extension element 21 and the first scissor blade 14 terminate on their side facing the shaft 1 in two arms 23 extending parallel to each other and accommodating between them a bearing shaft 24. There is pivotably mounted on this bearing shaft a lever 25, which, in each case, dips into the space between the arms 23. The other ends of the levers 25 are pivotably connected to bearing studs 26 at the free end of the push-pull rod 2. The two scissor blades 14 and 15 are thereby pivoted between the open position and the closed position as a result of pushing forward and pulling back the push-pull rod 2, i.e., the cutting edges 16 and 19 can be brought closer together or moved further apart by displacing the push-pull rod 2.

The push-pull rod 2 consists of metal and is connected to a pole of a voltage source. It penetrates the holder 4, is insulated by the insulating coating 13 on the inside thereof and connects the voltage source via one of the levers 25 and the corresponding arms 23 to the first scissor blade 14.

However, there is no electrical connection to the second scissor blade 15, and, in particular, to the metallic support blade 18 because the metallic extension element 21, which is electrically conductively connected to the push-pull rod 2, is electrically separated from both the support blade 18 and the bearing shaft 12 by the ceramic shaped body 17 and the sleeve 20 integrally formed thereon.

On the other hand, the sleeve 20 also separates the bearing shaft 24 from the first scissor blade 14, but there is an electrical connection between the support blade 18 and the bearing shaft 12 and likewise between the bearing shaft 12 and the holder 4, which, in turn, is electrically conductively connected to the shaft 1. The shaft 1 is connected to the second pole of the voltage source so that in this way an electrical connection is established from the voltage source to the support blade 18. One thus obtains two electrodes in the form of the first scissor blade 14 and in the form of the support blade 18 of the second scissor blade 15, which are electrically separated from each other by the shaped body 17, but when cutting tissue 27 positioned between the scissor blades, they come so close together that a current which causes hemostasis of the tissue (FIG. 3) can flow through the tissue.

The ceramic shaped body 17 is permanently connected to the support blade 18 against whose surface it rests, for example, by means of an adhesive or, in particular, by a soldered connection. In the area outside of the bearing point the soldering is preferably carried out as a soft solder, in the area of the bearing point, however, as a hard solder.

The strength of the connection between shaped body 17 and support blade 18 is further increased by the shaped body 17 carrying on its outer side a longitudinal rib which extends over the entire length thereof and fits into a complementary longitudinal groove in the support blade 18. In this way, a positive locking connection is obtained between shaped body 17 and support blade 18 so that also high torques can be transmitted without any risk via this composite body.

The extension element 21 rests with an end edge 30 against a corresponding stop edge 31 of the shaped body 17 so that in addition to the solder connection, torques can also be transmitted via these stop surfaces. The strength of the entire scissor blade is thereby also increased.

What is claimed is:

1. Surgical bipolar scissors with two scissor blades pivotable relative to each other, the first of which consists of an electrically conductive material, and the second of which consists of an electrically insulating material on a side thereof facing the first scissor blade, but of an electrically conductive material on a side thereof facing away from the first scissor blade, wherein:

the second scissor blade comprises a ceramic shaped body in the form of a complete scissor blade extending beyond a bearing point of the two scissor blades, a metallic support blade likewise extending beyond the bearing point rests against the outer side of the shaped body over the surface thereof, the shaped body and the support blade are permanently connected to each other at their contact surface, and the shaped body forms a bearing sleeve which surrounds a bearing shaft of the two scissor blades and extends through the first scissor blade.

2. Bipolar scissors as defined in claim 1, wherein the shaped body and the support blade comprise projections and recesses which engage one another in a positive locking manner.

3. Bipolar scissors as defined in claim 2, wherein the shaped body carries a longitudinal rib which engages in a longitudinal groove of the support blade in a positive locking manner.

4. Bipolar scissors as defined in claim 1, wherein a metal extension element rests against the shaped body in the area of the bearing point thereof on the side thereof opposite the support blade and is connected to the shaped body, said extension element being, in turn, connected to a part of a pivot mechanism for pivoting the scissor blades.

5. Bipolar scissors as defined in claim 4, wherein the shaped body and the extension element comprise projections and recesses which engage one another in a positive locking manner.

6. Bipolar scissors as defined in claim 1, wherein the shaped body and the support blade are soldered to each other.

7. Bipolar scissors as defined in claim 6, wherein the shaped body and the support blade are connected to each other in the cutting area by a soft solder, and in the area of the bearing point by a hard solder.

* * * * *